United States Patent [19]
Cassidy

[11] Patent Number: 5,435,196
[45] Date of Patent: Jul. 25, 1995

[54] IMMERSION PROBE FOR COLLECTING SLAG SAMPLES

[75] Inventor: John E. Cassidy, Churchville, Pa.

[73] Assignee: Heraeus Electro-Nite International N.V, Houthalen, Belgium

[21] Appl. No.: 171,808

[22] Filed: Dec. 22, 1993

[51] Int. Cl.$^6$ .............................................. G01N 1/10
[52] U.S. Cl. ................... 73/863.11; 73/DIG. 9
[58] Field of Search .......... 73/64.56, 863.11, 863.82, 73/864.31, 864.53, 864.71, 866, DIG. 9

[56]     References Cited
U.S. PATENT DOCUMENTS

| | | | |
|---|---|---|---|
| 3,643,508 | 2/1972 | Schneider | 73/863.11 |
| 3,717,034 | 2/1973 | Dukelow et al. | 73/DIG. 9 |
| 3,791,219 | 2/1974 | Falk | 73/DIG. 9 |
| 3,888,123 | 6/1975 | Kuntziger et al. | 73/863.11 |
| 4,941,364 | 7/1990 | Haughton | 73/DIG. 9 |
| 5,060,530 | 10/1991 | Haughton | 73/864.53 |

FOREIGN PATENT DOCUMENTS

0127278  7/1959  U.S.S.R. .................... 73/DIG. 9

*Primary Examiner*—Richard E. Chilcot, Jr.
*Assistant Examiner*—George M. Dombroske
*Attorney, Agent, or Firm*—Panitch Schwarze Jacobs & Nadel

[57]    ABSTRACT

An immersion probe includes an elongated probe body having an axis, an external surface and a first end for immersion into a bath of molten metal, the molten metal bath having a slag layer on the upper surface thereof. The first end of the probe body includes a device for detecting a characteristic of the molten metal. The immersion probe further includes a chill member movably supported by and at least partially surrounding a portion of the external surface of the probe body. The chill member is freely axially movable with respect to the probe body. A buoyancy member engages the chill member. The buoyancy member has a density such that upon immersion of the first end of the probe into the molten metal bath the chill member moves axially with respect to the probe body so that the chill member is positioned within the slag layer for chilling and collecting a slag sample. One or more stop members may be provided on the probe body for limiting movement of the chill member.

22 Claims, 6 Drawing Sheets

IMMERSION PROBE FOR COLLECTING SLAG SAMPLES

FIELD OF THE INVENTION

The present invention relates to probes for detecting characteristics of a molten metal and, more particularly, to such a probe which is also employed for collecting a sample of molten slag floating on the surface above the molten metal.

BACKGROUND OF THE INVENTION

In most molten metal refining processes, including processes for making steel, aluminum, brass and the like, a molten slag is produced. Because molten slag generally has a density which is lower than the molten metal, it generally floats and accumulates above the upper surface of the molten metal within a processing vessel. The slag provides for essential metallurgical functions such as the absorption of certain elements desired to be removed from the molten metal or the creation of an environment in which elements may be added to the molten metal by methods such as oxide reduction in the slag and may be later transferred to the metal. In other applications the slag serves as a reaction site which facilitates certain chemical reactions which are necessary or desirable in order to efficiently process the molten metal from its initial, crude state to a finished product. In the metal making industry, it is important to monitor the chemical and/or metallurgical composition of the refined slag in order to effectively monitor the molten metal processing. Thus, it is necessary to efficiently collect and timely analyze the slag in order to properly control the metal refining process.

A traditional method for obtaining a sample of metal refining slag from a molten metal bath in a processing vessel is to immerse a metal object, such as a pipe, a metal spoon, a metal chain or the like into the slag for a predetermined relatively short period of time. Because of temperature variations, a layer of the molten slag is chilled onto the cooler metal object so that upon removal of the metal object from the processing vessel, the solid slag may be conveniently broken away from the metal object, collected and promptly analyzed using known analytical methods and techniques.

It is also common in the metal producing industry to monitor various other qualities of the molten metal in a processing vessel such as temperature, viscosity, temperature of solidification (liquidest arrest temperature) and carbon, oxygen and other component content. Many different types of devices or probes have been developed and used for this purpose. Many such devices have a common feature, namely they generally employ a hollow cardboard tube which serves as a probe body for supporting one or more sensors and/or samplers to allow the sensors and/or samplers to be inserted into the molten metal at a desired depth below the refining slag to obtain the necessary data and/or samplers. Because of the hostile environment in which the sensors operate, most such sensors are disposable, having a life on the order of only a few seconds. In general, the cardboard tube supporting the sensors is continually combusted during the time that the sensors are in the molten metal bath.

Traditionally, such disposable sensors are inserted into the molten metal bath manually by an operator using steel pipes which have been adapted with electrical contacts and wiring for electrically passing signals received from the sensors mounted on the first or immersion end of the cardboard tube. In other applications the manual, operator immersion of the expendable sensor is replaced with a mechanical manipulator or pantograph which interconnects with the distal or upper end of the cardboard tube and is employed for automatically lowering the tube and sensors into the molten metal bath at a predetermined immersion depth.

It has become well-known to secure a generally cylindrical metal object to the cardboard tube on a immersion probe for the purpose of collecting a sample of the slag as the sensor measurements are made. Typically such metal objects, such as metal tubes or metal coils, are permanently secured to the cardboard tube at a stationary position, generally a predetermined distance from the first or measurement end of the cardboard tube or probe body. In this manner, when the probe body is inserted or immersed into the molten metal bath for making the required measurement, a sample of the slag can be simultaneously obtained and recovered when the probe body is removed from the metal bath.

While this method of obtaining slag samples can be useful in some applications, it is sometimes difficult to use because it requires that the operator very carefully judge the precise location of the slag and its depth so that the metal object used for collecting the sample of the slag is, in fact, maintained in the slag layer and does not pass through the slag into the molten metal below. It is often difficult for an operator to make such a judgment because of the bright, sometimes blinding, light emitted by molten materials at high temperature. It is even more difficult for an operator to judge the correct placement of the slag collecting metal object because the volume of molten metal in a refining vessel or transferring container is not generally reproducible from batch to batch so that the location (depth) of the slag layer also varies from batch to batch. When an automatic or pantograph immersion system is employed, constant adjustment is required to adapt to the changing volumes of the molten metal in order to obtain proper slag samples. If the slag collecting metal object is immersed too deeply, the slag collecting object can be destroyed by the molten metal. If the slag collecting metal object is not immersed deeply enough to be within the slag layer, either insufficient slag is collected or no slag is collected at all.

The present invention overcomes the problems of the prior art slag sample collecting methods by eliminating the need for an operator determining the exact depth of immersion or exact location for fixing the slag collecting metal object by allowing the slag collecting metal object to "float" or move up and down the cardboard tube of the immersion probe. The movement of the slag collecting metal object assures that the slag collecting metal object is at a position of maximum exposure to the slag while keeping the slag collecting metal object out of the molten metal. The range of movement of the slag collecting metal object is contained at the lowermost or first and uppermost or distal ends of the probe body. Optimum buoyancy is obtained by the combination of two materials, a slag collecting or chill material, generally metal and a second material of a density less than the density of the molten metal. In this manner, the average density of the resulting combination of the two materials is less than the density of the molten metal for any given type of metal and greater than the density of the refining slag to be sampled.

SUMMARY OF THE INVENTION

Briefly stated, the present invention is an improvement in an immersion probe, including an elongated probe body having an axis, an external surface and a first end for immersion into a bath of molten metal, the molten metal bath having a slag layer on the upper surface thereof. The first end of the probe body includes means for detecting a characteristic of the molten metal. The improvement comprises a chill member movably supported by and at least partially surrounding a portion of the external surface of the probe body. The chill member is axially movable with respect to the probe body. A buoyancy member is provided for engaging the chill member. The buoyancy member has a density such that upon immersion of the first end of the probe into the molten metal bath, the chill member moves axially with respect to the probe body so that the chill member is positioned within the slag layer for chilling and collecting a slag sample. In a preferred embodiment, first and second stop members are provided on the probe body for limiting movement of the chill member.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF PREFERRED EMBODIMENTS

Figure 1:
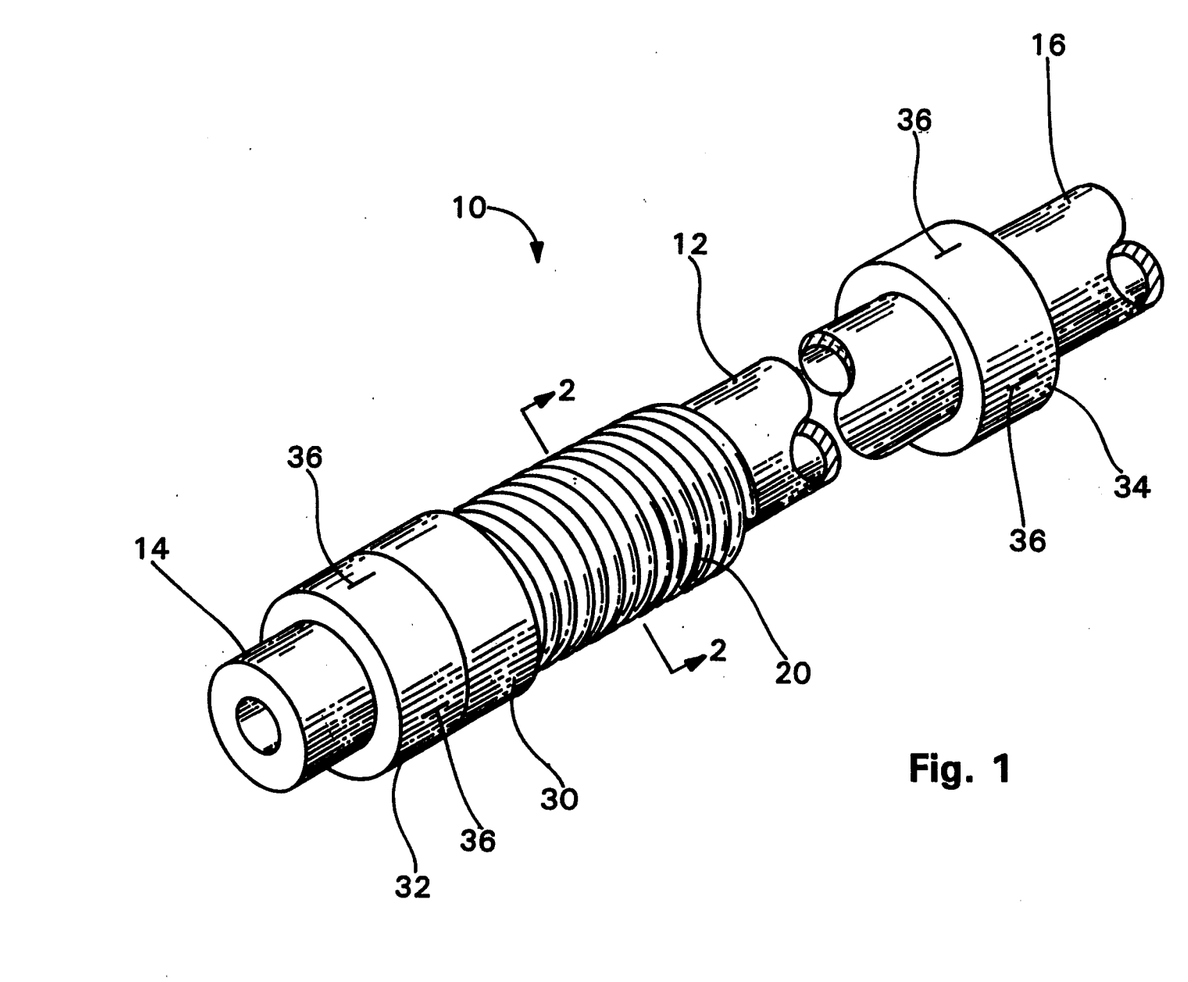
FIG. 1 is a schematic perspective view, partially broken away of an immersion probe in accordance with a first embodiment of the present invention.
Figure 2:
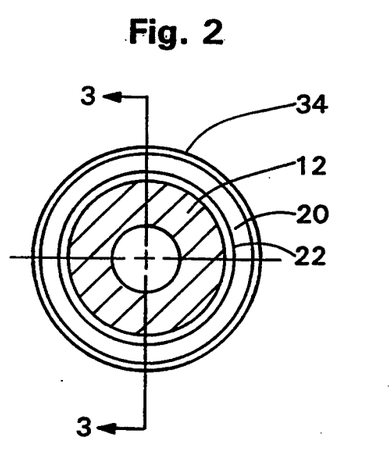
FIG. 2 is a sectional view of a portion of the immersion probe taken along line 2—2 of FIG. 1.
Figure 3:
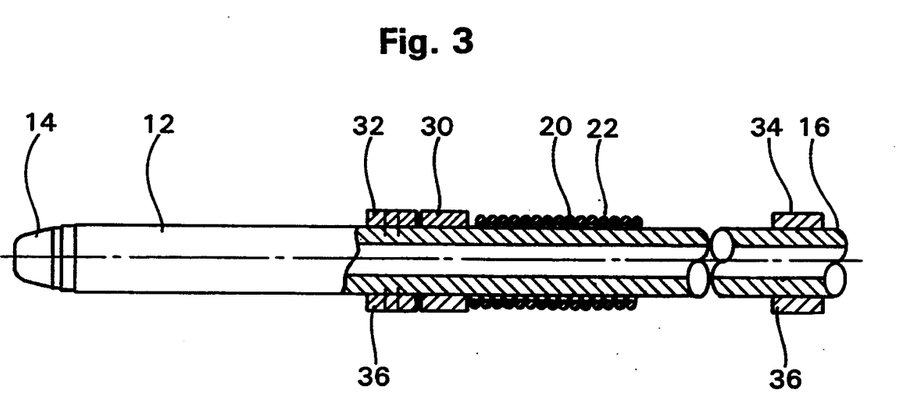
FIG. 3 is a sectional view of a portion of the immersion probe taken along line 3—3 of FIG. 2.

Referring to the drawings, wherein like numerals are used to indicate like elements throughout the several figures, there is shown in FIGS. 1–3 a schematic perspective view and two sectional views of an immersion probe 10 in accordance with a first embodiment of the present invention. The probe 10, in the present embodiment, includes a generally elongated generally cylindrical probe body 12 having a first end 14 (typically the bottom end) for immersion into a molten metal bath (not shown) and a second end 16 which is coupleable to a support means (not shown). The support means which is coupled to the second end of the probe body may be a manually operable support means (discussed above) or an automated support means such as a pantograph. As used herein, the term "molten metal bath" will be understood to mean the molten metal bath environment including the molten metal and the slag layer that typically accumulates on or around the top or upper surface of the molten metal. The metal which is molten may be steel, aluminum or any other type of metal produced in a processing vessel in a molten form.

The probe body 12 illustrated in FIG. 1 is typical of immersion probes generally known in the art and being of the multi-lance type. However, it should be clearly understood that the probe body 12 may include other configurations and designs for immersion probes for use in detecting one or more characteristics of a molten metal.

The probe body 12, in the present embodiment, is comprised of an elongated cardboard tube. The cardboard tube may be of any length and/or of any desired diameter and the cardboard may have any desired thickness for a particular use or application. The probe body 12 may also be made of any other material including quartz, ceramic, ceramic fiber, castible refractory or other refractory materials (commonly known as non-splash materials) known in the art for manufacturing immersion probe bodies intended for use in molten metal baths. The first end 14 of the probe body 12 may comprise similar, but not necessarily the same materials, as a remainder of the probe body 12. The first end 14 includes means for detecting one or more characteristics of the molten metal. Such detection means or devices may include, but are not limited to, thermocouple devices, devices for measuring certain element contents and devices for determining solidification temperatures. The type and number of detection devices within the first end 14 of the probe body 12 may vary from probe to probe depending upon the particular characteristics desired to be determined or measured using the immersion probe 10. It will be appreciated by those skilled in the art that the type and number of such devices is not meant to be a limitation on the present invention.

The present invention is comprised of a slag collecting apparatus which moves up and down along the probe body 12 in order to consistently obtain and collect a sample of the slag regardless of the depth that the probe 10 is immersed into in a molten metal bath. In the present embodiment, the apparatus comprises a chill member 20 movably supported by and at least partially surrounding the external surface of the probe body 12. The chill member 20 may be of a different shape, such as rectangular, if desired, and may not completely surround the probe body 12. The chill member 20 as shown in FIGS. 1–3 includes an interior surface 22 which is generally cylindrical with a diameter at least slightly greater than the diameter of the external surface of the probe body 12. In this manner, the chill member 20 fits loosely around the probe body 12 and may freely move axially along the probe body 12. In the present embodiment, the chill member 20 is a metal coil of a type well-known to those of ordinary skill in the art. The metal used to form the chill member 20 is the same as or is compatible with the molten metal with which the probe 10 is used. For example, if the molten metal in the molten metal bath is steel, the chill member 20 is steel.

A buoyancy member 30 engages one end of the chill member 20. The buoyancy member 30 in the present embodiment is generally tubular with an inner diameter which is at least slightly greater than the diameter of the external surface of the probe body 12. In this manner, the buoyancy member 30 fits loosely around the probe body 12 and may also freely move axially along the probe body 12 in a manner which will hereinafter be described. The buoyancy member 30 may be of a different shape if desired and need not completely surround the probe body 12.

Figure 4A:
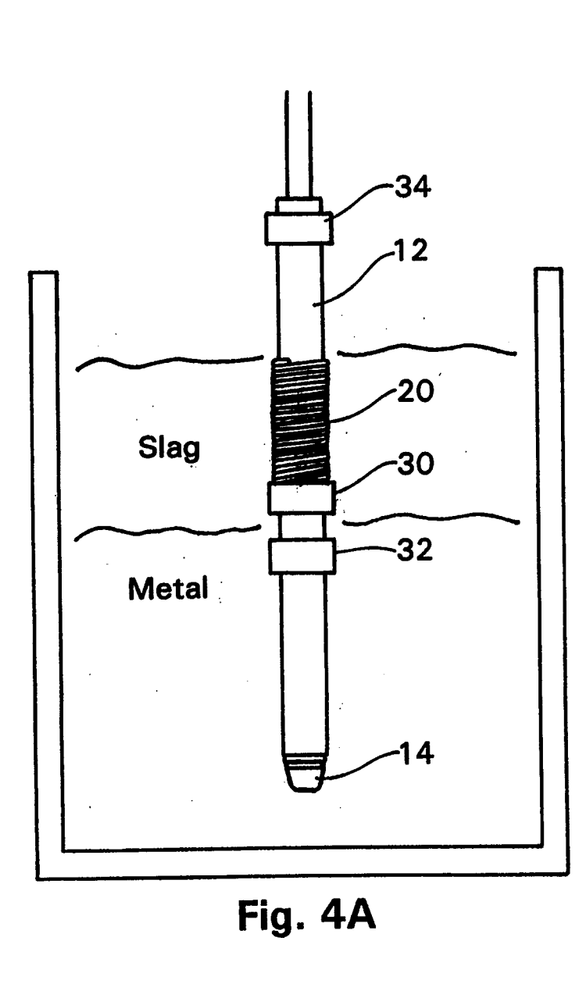
FIGS. 4A and 4B are diagrammatic illustrations of the functioning of the slag collecting portion of the immersion probe of FIG. 1 immersed into molten metal baths of differing depths.
Figure 4B:
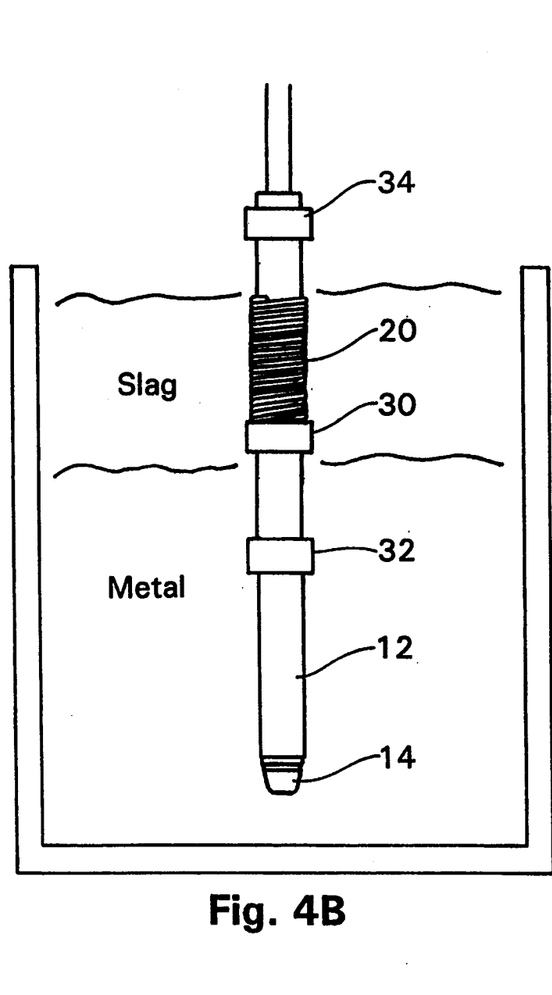

The present invention is employed for properly positioning the chill member (slag collecting object) in the slag when the immersion probe 10 is immersed into a molten metal bath. In order to achieve this result, in the present embodiment, the buoyancy member 30 is formed of a material which has a density which is substantially less than the density of the molten metal. In the illustrated embodiment, the buoyancy member 30 is made of cardboard but it could be made of wood, compressed wood, fiberboard, a low-density ceramic, fibrous ceramic plastic or any other such material having the proper density. In this manner, upon immersion of the first end 14 of the probe body 12 into a molten metal bath, the buoyancy member 30 "floats" on the upper surface of the molten metal. In order to float in this manner the buoyancy member 30 slides axially upwardly along the probe body 12 as the probe 10 is lowered into the molten metal. In the embodiment illustrated in FIGS. 1-3, the buoyancy member 30 is positioned between the chill member 20 and the first end 14 of the probe body 12 and the outer diameter of the buoyancy member 30 is greater than the outer diameter of the chill member 20. Thus, upward movement of the buoyancy member 30, i.e., away from the first end 14 of the probe body 12, results in corresponding upward movement of the chill member 20. In this manner, as best illustrated in FIGS. 4A and 4B, the floatation of the buoyancy member 30 on the upper surface of the molten metal causes the chill member 20 to automatically be positioned within the slag layer for chilling and collecting a slag sample in the manner known in the art. As illustrated in FIGS. 4A and 4B, the present invention functions to maintain the chill member 20 within the slag layer regardless of the depth of immersion of the first end 14 of the probe body 12.

The immersion probe 10 further includes a first stop member 32 secured to the probe body 12 proximate the first end 14 of the probe body 12. The stop member 32, in the present embodiment, is a generally cylindrical, collar-like member, having an inner diameter which is substantially the same as the diameter of the external surface of the probe body 12. Preferably the first stop member 32 is made of cardboard or a similar type of material. The stop member 32 is secured or fixed to the probe body 12 utilizing a plurality of metal staples 36 which are spaced around the periphery of the stop member 32 and extend into the probe body 12. The outer diameter of the stop member 32 is substantially the same as the outer diameter of the buoyancy member 30. In this manner, the stop member 32 limits movement of the buoyancy member 30 and the chill member 20 toward the first end 14 of the probe body 12, thereby effectively preventing the buoyancy member 30 and the chill member 22 from falling off of the first end 14 of the probe body 12.

The immersion probe 10 further includes a second stop member 34 secured to the probe body 12 at a predetermined distance from the first end 14 of the probe body 12. The second stop member 34, in the present embodiment, is structurally the same as the first stop member 32 and the second stop member 34 is secured to the probe body 12 utilizing staples 36 in substantially the same manner that the first stop member 32 is secured to the probe body 12. The second stop member 34 limits movement of the chill member 20 and the buoyancy member 30 upwardly, away from the first end 14 of the probe body 12. Preferably, the second stop member 34 is spaced far enough away from the first stop member 32 so that the chill member 20 and the buoyancy member 30 are permitted to move along the probe body 12 a distance sufficient to position the chill member 20 in the slag layer regardless of the depth that the first end 14 of the probe body 12 is immersed into the molten metal bath. The actual distance will vary depending upon the type of metal in the molten metal bath, the depth of the processing vessel and other factors. Typically, an immersion probe 10 used in steel making could have an overall length of eight feet or more in which case the distance between the first stop member 32 and the second step member 34 is preferably in the range of about six feet. While, in the present embodiment, stop members 32 and 34 are constructed of cardboard, they can be made of a variety of other materials such as wood, fiberboard, low density ceramic, fibrous ceramic, plastic and/or any other material capable of surviving immersion into the molten metal bath.

The immersion probe 10 formed in accordance with the present invention is advantageous in that it permits a single probe configuration to be used regardless of variations in the volume or depth of the molten metal bath. In addition, the same configuration can be used in different metal processing industries thereby allowing high volume manufacturing techniques and the resulting lowering of assembly costs. The present invention also permits the average density of the chill member 20 and the buoyancy member 30 to vary based upon the materials employed in order to accommodate various end applications in accordance with the densities of the refined slags and molten metal baths within various metal refining industries. The present invention can be used with virtually any type of sensor known to those of ordinary skill in the art either utilizing a standard cardboard type probe or any type non-splash probe.

Figures 5A, 5B, 5C:
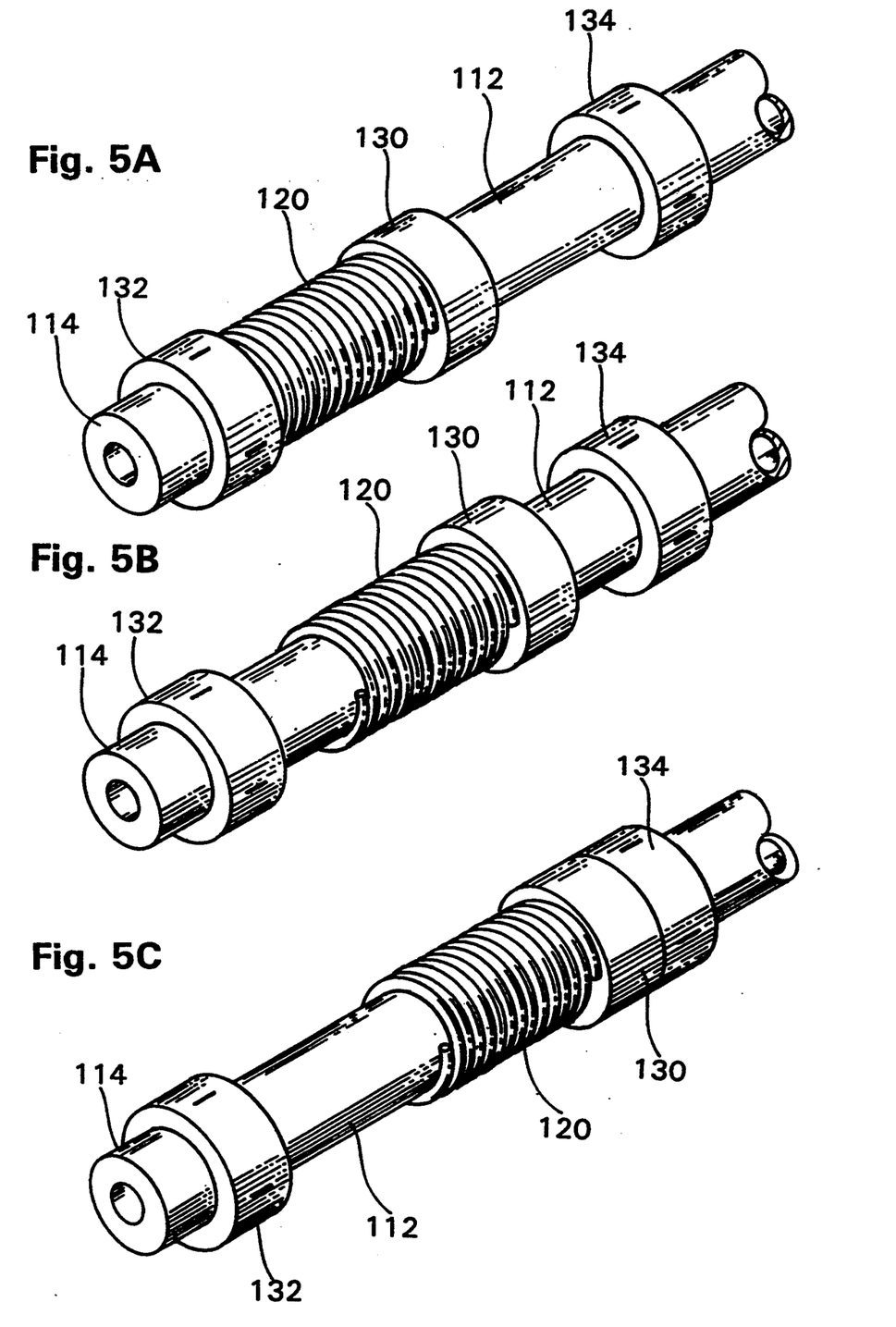
FIGS. 5A, 5B and 5C are schematic perspective views which show an alternate embodiment of the invention.

FIGS. 5A, 5B and 5C illustrate the functioning of an alternate embodiment of the invention. The embodiment shown in FIGS. 5A, 5B and 5B is substantially the same as the embodiment shown in FIGS. 1-3 and includes a probe body 112, a chill member 120, a buoyancy member 130 and first and second stop members 132 and 134. However, unlike the embodiment of FIGS. 1-3, in the embodiment shown in FIGS. 5A, 5B and 5C, the chill member 120 is positioned between the first stop member 132 and the buoyancy member 130 with the buoyancy member 130 being attached or secured to the end of the chill member 120. The density of the buoyancy member 130 is selected so that the average density of the combination of the chill member 120 and the buoyancy member 130 is less than that of the molten metal and greater than or equal to the density of the slag. In this manner, the buoyancy member 130 effectively pulls the chill member 120 upwardly, away from the first end 114 of the probe body 112 as opposed to pushing the chill member 20 upwardly as is does in connection with the embodiment of FIGS. 1-3. FIGS. 5B and 5C illustrate the movement of the buoyancy member 130 with the chill member 120 attached thereto. The length of the probe body 112 is shown as being relatively short in FIGS. 5A, 5B and 5C for the purpose of illustrating the present invention, but it should be understood by those skilled in the art that the actual length of the probe body 112 may be greater than or less than the illustrated length.

Figure 6:
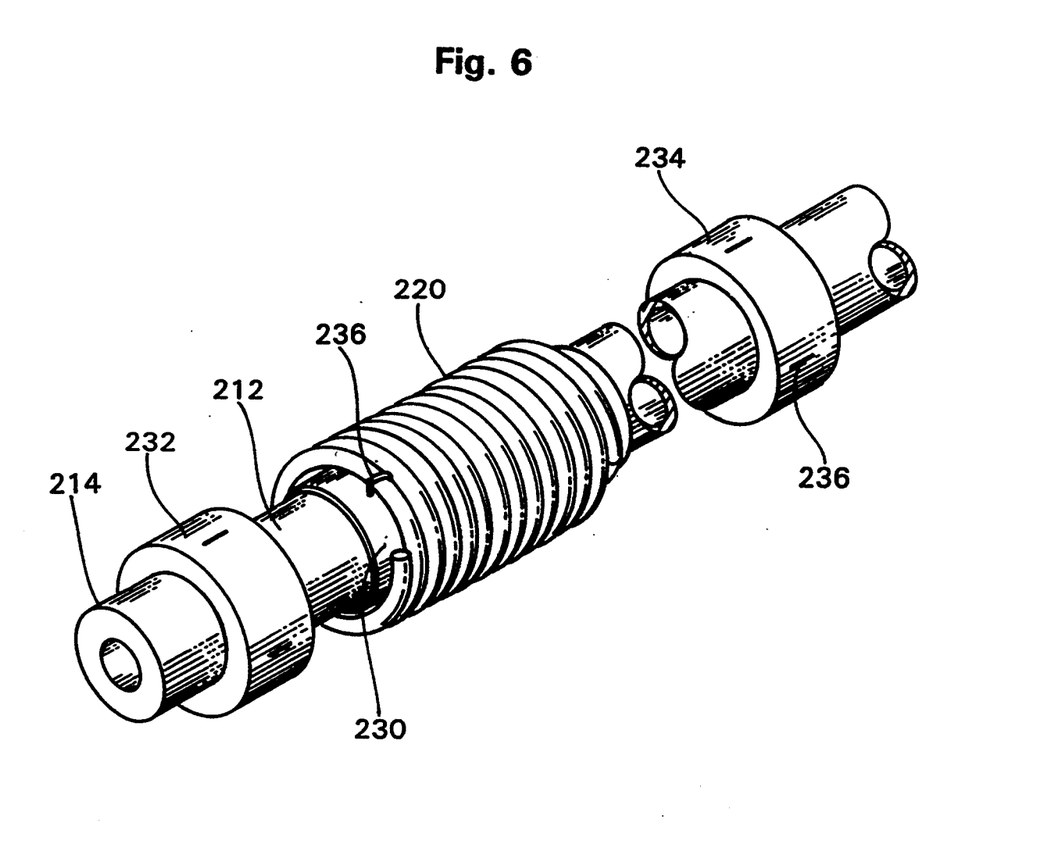
FIG. 6 is a schematic perspective view which shows another alternate embodiment of the invention.

FIG. 6 shows yet another embodiment of the present invention. In the embodiment shown in FIG. 6, the probe body 212, first and second stop members 232 and 234 and the chill member 220 are substantially the same as the corresponding components of the embodiment shown in FIGS. 1–3. However, in the embodiment shown in FIG. 6, the buoyancy member 230 is different. The buoyancy member 230 is a generally tubular member which has an inner diameter at least slightly greater than the outer diameter of the probe body 212 but has an outer diameter which is the same or slightly less than the inner diameter of the chill member 220. The chill member 220, the buoyancy member 230 and the probe body 212 are concentric with the buoyancy member 230 being positioned between the probe body 212 and the chill member 220. As with the above-described embodiments, the density of the buoyancy member 230 is selected so that the average density of the combination of the buoyancy member 230 and the chill member 220 is less than the density of the molten metal so that the combined buoyancy member 230 and chill member 220 float when immersed into the molten metal to thereby position the chill member within the slag layer on top of the molten metal. The chill member 220 may be secured to the buoyancy member 230 utilizing the one or more staples 236 or in any other manner known to those of ordinary skill in the art.

Figures 7A, 7B, 7C:
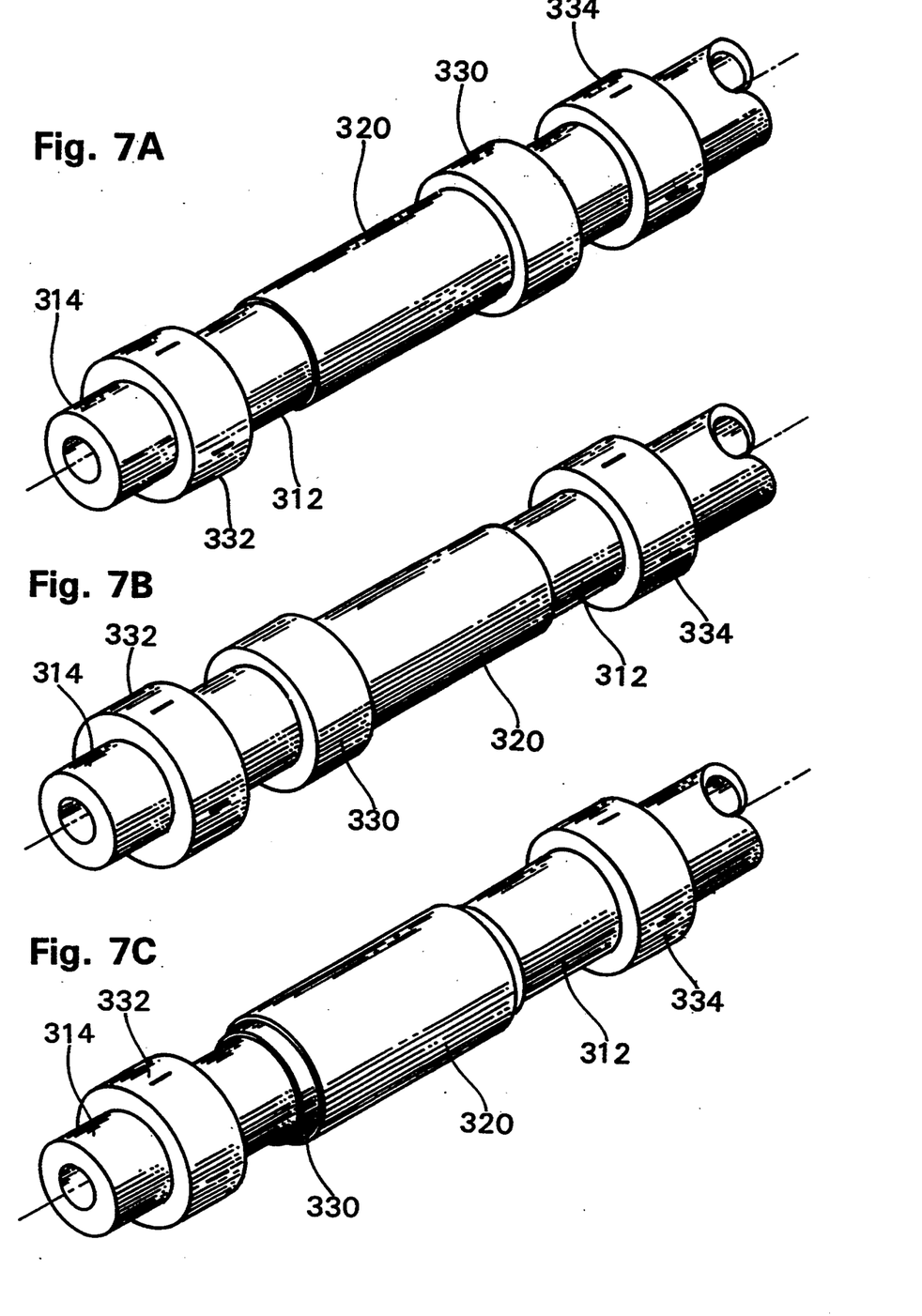
FIGS. 7A, 7B and 7C are schematic perspective views which illustrate three other but similar embodiments of the invention.

FIGS. 7A, 7B and 7C illustrate three aspects of yet another embodiment of the present invention. In FIGS. 7A, 7B and 7C, the probe body 312 and the stop members 332 and 334 are the same as in the above described embodiments. However, the chill member 320, is a generally cylindrical member rather than the coil shown in the above-described embodiments. 10 FIG. 7B illustrates an embodiment substantially the same as that of FIGS. 1–3 but with the cylindrical chill member 320. FIG. 7A illustrates an embodiment which is substantially the same as the embodiment shown in FIGS. 5A, 5B and 5C but with a cylindrical chill member 220. Correspondingly, FIG. 7C illustrates an embodiment which is substantially the same as the embodiment disclosed in FIG. 6 but again with the chill member 320 being cylindrical.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. In an immersion probe including an elongated probe body having an axis, an external surface and a first end for immersion into a bath of molten metal, the molten metal bath having a slag layer on the upper surface thereof, the first end of the probe body including means for detecting a characteristic of the molten metal, the improvement comprising:
   a chill member movably supported by and at least partially surrounding a portion of the external surface of the probe body, the chill member being axially movable with respect to the probe body; and
   a buoyancy member engaging the chill member, the buoyancy member having a density such that upon immersion of the first end of the probe into the molten metal bath, the chill member moves axially with respect to the probe body so that the chill member is positioned within the slag layer for chilling and collecting a slag sample.

2. The immersion probe as recited in claim 1, wherein the portion of the external surface of the probe body is generally cylindrical and the chill member includes an interior surface which is generally cylindrical with a diameter at least slightly greater than the diameter of the external surface of the portion of the probe body.

3. The immersion probe as recited in claim 2, wherein the chill member comprises a metal coil.

4. The immersion probe as recited in claim 2, wherein the chill member comprises a metal tube.

5. The immersion probe as recited in claim 2, wherein the chill member comprises a plurality of metal disks.

6. The immersion probe as recited in claim 2, wherein the buoyancy member is generally tubular and surrounds the portion of the probe body, the buoyancy member having an inner diameter which is at least slightly greater than the diameter of the external surface of the portion of the probe body, the buoyancy member being positioned between the chill member and the first end of the probe body.

7. The immersion probe as recited in claim 2, wherein the buoyancy member is generally tubular and surrounds the portion of the probe body, the buoyancy member having an inner diameter which is at least slightly greater than the diameter of the external surface of the portion of the probe body, the chill member being positioned between the buoyancy member and the first end of the probe body.

8. The immersion probe as recited in claim 2, wherein the buoyancy member is generally tubular and is concentric with the chill member, the buoyancy member being positioned between the chill member and the portion of the probe body.

9. The immersion probe as recited in claim 1, wherein the buoyancy member has a density which is substantially less than the density of the molten metal so that upon immersion of the first end of the probe body into the molten metal bath, the buoyancy member floats on top of the molten metal to position the chill member in the slag layer.

10. The immersion probe as recited in claim 1, wherein the buoyancy member has a density which is such that the combination of the buoyancy member and the chill member has an average density which is less than the density of the molten metal so that upon immersion of the first end of the probe body into the molten metal bath, the buoyancy member and the chill member float on the top of the molten metal to position the chill member in the slag layer.

11. The immersion probe as recited in claim 1, further including a first stop member secured to the probe body proximate the first end of the probe body for limiting movement of the chill member toward the first end of the probe.

12. The immersion probe as recited in claim 11, further including a second stop member secured to the probe body distal to the first end of the probe body for limiting movement of the chill member away from the first end of the probe body.

13. The immersion probe as recited in claim 12, wherein the first and second stop members are spaced far enough apart on the probe body to permit the chill member to move along the probe body a distance sufficient to position the chill member in the slag layer regardless of the depth that the first end of the probe body is immersed into the molten metal bath.

14. The immersion probe as recited in claim 1, wherein the probe body is comprised of a cardboard tube.

15. The immersion probe as recited in claim 1, wherein the probe body is comprised of a non-splash material.

16. In an immersion probe including an elongated generally cylindrical probe body having an axis, an external surface, and a first end for immersion into a bath of molten metal, the molten metal bath having a molten metal slag layer on the upper surface thereof, the first end of the probe body including means for detecting a characteristic of the molten metal, the improvement comprising:

a generally cylindrical chill member movably supported by and at least partially surrounding a portion of the external surface of the probe body, the chill member having an interior surface with a diameter at least slightly greater than the diameter of the exterior surface of the portion of the probe body so that the chill member is axially movable with respect to the probe body;

a generally tubular buoyancy member movably supported by and surrounding the portion of the external surface of the probe body, the buoyancy member including an interior surface with a diameter at least slightly greater than the diameter of the exterior surface of the portion of the probe body so that the buoyancy member is axially movable with respect to the probe body, the buoyancy member engaging the chill member so that the two members move together, the buoyancy member having a density such that upon immersion of the first end of the probe into the molten metal bath, the members move relative to the probe body such that the chill member is positioned within the slag layer for chilling and collecting a slag sample;

a first stop member secured to the probe body proximate the first end of the probe body for limiting movement of the chill member and the buoyancy member toward the first end of the probe body; and a second stop member secured to the probe body distal to the first end of the probe body for limiting movement of the chill member and the buoyancy member away from the first end of the probe body.

17. The immersion probe as recited in claim 16, wherein the buoyancy member is formed of cardboard.

18. The immersion probe as recited in claim 17, wherein the first and second stop members are generally tubular members formed of cardboard.

19. The immersion probe as recited in claim 18, wherein the chill member comprises a metal coil.

20. The immersion probe as recited in claim 18, wherein the chill member comprises a metal tube.

21. The immersion probe as recited in claim 18, wherein the probe body is comprised of a cardboard tube.

22. The immersion probe as recited in claim 18, wherein the probe body is comprised of a non-splash material.

* * * * *